United States Patent
DiMauro et al.

(10) Patent No.: US 8,906,033 B2
(45) Date of Patent: Dec. 9, 2014

(54) CERVICAL MOTION DISC INSERTER

(75) Inventors: Thomas M. DiMauro, Southborough, MA (US); Edward B. Zalenski, Lakeville, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 737 days.

(21) Appl. No.: 12/414,591

(22) Filed: Mar. 30, 2009

(65) Prior Publication Data

US 2010/0249795 A1 Sep. 30, 2010

(51) Int. Cl.
*A61B 17/58* (2006.01)
*A61B 17/60* (2006.01)
*A61F 2/00* (2006.01)
*A61F 2/46* (2006.01)

(52) U.S. Cl.
CPC ....... *A61F 2/4611* (2013.01); *A61F 2002/4624* (2013.01); *A61F 2002/4622* (2013.01); *A61F 2002/4628* (2013.01)
USPC ........................... 606/99; 606/206; 623/17.16

(58) Field of Classification Search
USPC ............ 606/99, 206; 269/96; 73/1.12; 81/54, 81/97, 103, 126–127, 146, 321–323, 380; 623/17.16
See application file for complete search history.

(56) References Cited

U.S. PATENT DOCUMENTS

| | | | |
|---|---|---|---|
| 132,057 A * | 10/1872 | Cooper et al. | 81/146 |
| 1,539,987 A * | 6/1925 | Bell | 81/129.5 |
| 3,141,583 A | 7/1964 | Mpel | |
| 3,752,161 A | 8/1973 | Bent | |
| 3,835,860 A | 9/1974 | Garretson | |
| 4,367,746 A | 1/1983 | Derechinsky | |
| 4,512,345 A | 4/1985 | Green | |
| 4,592,347 A * | 6/1986 | Mahruki | 606/206 |
| 4,759,766 A | 7/1988 | Buettner-Janz et al. | |
| 5,018,412 A * | 5/1991 | Wylie, III | 81/111 |
| 5,222,973 A * | 6/1993 | Sharpe et al. | 606/206 |
| 5,236,460 A | 8/1993 | Barber | |
| 5,258,031 A | 11/1993 | Salib et al. | |
| 5,300,081 A | 4/1994 | Young | |
| 5,314,477 A | 5/1994 | Marnay | |
| 5,360,430 A | 11/1994 | Lin | |
| 5,370,697 A | 12/1994 | Baumgartner | |
| 5,383,888 A * | 1/1995 | Zvenyatsky et al. | 606/206 |
| 5,401,269 A | 3/1995 | Buttner-Janz et al. | |
| 5,425,773 A | 6/1995 | Boyd | |

(Continued)

FOREIGN PATENT DOCUMENTS

| | | |
|---|---|---|
| EP | 333990 | 1/1989 |
| EP | 535973 | 10/1992 |

(Continued)

OTHER PUBLICATIONS

Krag et al., "An Internal Fixator for Posterior Application to Short Segments of the Thoacic, Lumbar, or Lumbosacral Spine," CLiN. Ortho. & Related Res. 203:75-98 (1986).

*Primary Examiner* — Andrew Yang
*Assistant Examiner* — Olivia C Chang
(74) *Attorney, Agent, or Firm* — Raymond N. Scott, Jr.

(57) ABSTRACT

A novel inserter for inserting a prosthetic cervical motion disc, wherein the distal end portion of the inserter features a pair of projections that are adapted to move slidably and transversely relative to one another (like a wrench) in order to engage a prosthetic cervical motion disc.

8 Claims, 13 Drawing Sheets

(56) References Cited

U.S. PATENT DOCUMENTS

| | | |
|---|---|---|
| 5,431,654 A | 7/1995 | Nic |
| 5,431,658 A | 7/1995 | Moskovich |
| 5,443,514 A | 8/1995 | Steffee |
| 5,458,641 A | 10/1995 | Ramirez Jimenez |
| 5,486,185 A * | 1/1996 | Freitas et al. ............... 606/142 |
| 5,505,732 A | 4/1996 | Michelson |
| 5,507,816 A | 4/1996 | Bullivant |
| 5,562,738 A | 10/1996 | Boyd |
| 5,591,170 A | 1/1997 | Spievack et al. |
| 5,676,701 A | 10/1997 | Yuan et al. |
| 5,683,465 A | 11/1997 | Shinn |
| 5,782,830 A | 7/1998 | Farris |
| 5,782,832 A | 7/1998 | Larsen et al. |
| 5,797,927 A | 8/1998 | Yoon |
| 5,851,207 A | 12/1998 | Cesarone |
| 5,873,886 A | 2/1999 | Larsen et al. |
| 5,895,428 A | 4/1999 | Berry |
| 5,899,941 A | 5/1999 | Nishijima |
| 5,931,849 A | 8/1999 | Desvignes |
| 5,938,678 A | 8/1999 | Zirps |
| 5,989,291 A | 11/1999 | Ralph et al. |
| 6,019,792 A | 2/2000 | Cauthen |
| 6,063,121 A | 5/2000 | Xavier et al. |
| 6,066,174 A * | 5/2000 | Farris ............... 606/206 |
| 6,099,550 A | 8/2000 | Yoon |
| 6,110,179 A | 8/2000 | Flivik |
| 6,113,605 A | 9/2000 | Storer |
| 6,113,637 A | 9/2000 | Gill |
| 6,146,421 A | 11/2000 | Gordon |
| 6,159,215 A | 12/2000 | Urbahns et al. |
| 6,174,311 B1 | 1/2001 | Branch |
| 6,179,874 B1 | 1/2001 | Cauthen |
| 6,227,079 B1 * | 5/2001 | Liu ................... 81/126 |
| 6,228,118 B1 | 5/2001 | Gordon |
| 6,261,296 B1 | 7/2001 | Aebi |
| 6,296,665 B1 | 10/2001 | Strnad et al. |
| 6,319,257 B1 * | 11/2001 | Carignan et al. ............. 606/99 |
| 6,328,746 B1 | 12/2001 | Gambale |
| 6,358,268 B1 | 3/2002 | Hunt |
| 6,368,350 B1 | 4/2002 | Erickson |
| 6,371,986 B1 | 4/2002 | Bagby |
| 6,375,682 B1 | 4/2002 | Fleischmann et al. |
| 6,395,034 B1 | 5/2002 | Suddaby |
| 6,416,551 B1 | 7/2002 | Keller |
| 6,439,439 B1 | 8/2002 | Rickard et al. |
| 6,440,142 B1 | 8/2002 | Ralph et al. |
| 6,440,168 B1 | 8/2002 | Cauthen |
| 6,517,544 B1 | 2/2003 | Michelson |
| 6,517,580 B1 | 2/2003 | Ramadan et al. |
| 6,520,996 B1 | 2/2003 | Manasas et al. |
| 6,524,312 B2 | 2/2003 | Landry et al. |
| 6,527,804 B1 | 3/2003 | Gauchet et al. |
| 6,540,785 B1 | 4/2003 | Gill |
| 6,562,074 B2 | 5/2003 | Gerbec |
| 6,579,320 B1 | 6/2003 | Gauchet et al. |
| 6,599,292 B1 | 7/2003 | Ray |
| 6,599,294 B2 | 7/2003 | Fuss |
| 6,599,295 B1 | 7/2003 | Tornier |
| 6,616,671 B2 | 9/2003 | Landry et al. |
| 6,648,891 B2 | 11/2003 | Kim |
| 6,652,533 B2 | 11/2003 | O'Neil |
| 6,652,534 B2 | 11/2003 | Zucherman et al. |
| 6,660,006 B2 | 12/2003 | Markworth et al. |
| 6,663,637 B2 | 12/2003 | Dixon |
| 6,692,501 B2 | 2/2004 | Michelson |
| 6,712,818 B1 | 3/2004 | Michelson |
| 6,740,087 B2 | 5/2004 | Knox |
| 7,011,683 B2 * | 3/2006 | Antonelli et al. ............. 623/10 |
| 7,608,080 B2 | 10/2009 | Shipp |
| 7,695,478 B2 * | 4/2010 | Ralph et al. ............. 606/99 |
| 8,123,757 B2 | 2/2012 | Zalenski |
| 2002/0035400 A1 | 3/2002 | Bryan et al. |
| 2002/0111679 A1 | 8/2002 | Zucherman et al. |
| 2002/0111681 A1 | 8/2002 | Ralph et al. |
| 2002/0111682 A1 | 8/2002 | Ralph et al. |
| 2002/0111683 A1 | 8/2002 | Ralph et al. |
| 2002/0111684 A1 | 8/2002 | Ralph et al. |
| 2002/0111685 A1 | 8/2002 | Ralph et al. |
| 2002/0111686 A1 | 8/2002 | Ralph et al. |
| 2002/0111687 A1 | 8/2002 | Ralph et al. |
| 2002/0116009 A1 | 8/2002 | Fraser et al. |
| 2002/0128714 A1 | 9/2002 | Manasas et al. |
| 2002/0128715 A1 | 9/2002 | Bryan et al. |
| 2002/0161366 A1 | 10/2002 | Robie et al. |
| 2002/0161375 A1 | 10/2002 | Ralph et al. |
| 2002/0173813 A1 | 11/2002 | Peterson |
| 2003/0033016 A1 | 2/2003 | Dees |
| 2003/0040802 A1 | 2/2003 | Errico |
| 2003/0060687 A1 | 3/2003 | Kleeman |
| 2003/0065395 A1 | 4/2003 | Ralph |
| 2003/0069586 A1 | 4/2003 | Errico |
| 2003/0069643 A1 | 4/2003 | Ralph et al. |
| 2003/0074066 A1 | 4/2003 | Errico |
| 2003/0074067 A1 | 4/2003 | Errico |
| 2003/0074068 A1 | 4/2003 | Errico |
| 2003/0074069 A1 | 4/2003 | Errico |
| 2003/0074070 A1 | 4/2003 | Errico |
| 2003/0074071 A1 | 4/2003 | Errico |
| 2003/0074072 A1 | 4/2003 | Errico |
| 2003/0074073 A1 | 4/2003 | Errico |
| 2003/0074074 A1 | 4/2003 | Errico |
| 2003/0074076 A1 | 4/2003 | Ferree |
| 2003/0078664 A1 | 4/2003 | Ralph et al. |
| 2003/0078665 A1 | 4/2003 | Ralph et al. |
| 2003/0078666 A1 | 4/2003 | Ralph et al. |
| 2003/0083747 A1 | 5/2003 | Winterbottom |
| 2003/0135275 A1 | 7/2003 | Garcia et al. |
| 2003/0135277 A1 | 7/2003 | Bryan et al. |
| 2003/0135278 A1 | 7/2003 | Eckman et al. |
| 2003/0149482 A1 | 8/2003 | Michelson |
| 2003/0171813 A1 | 9/2003 | Kiester |
| 2003/0187454 A1 | 10/2003 | Gill |
| 2003/0199872 A1 | 10/2003 | Markworth et al. |
| 2003/0216744 A1 | 11/2003 | Longhini |
| 2004/0102850 A1 * | 5/2004 | Shepard ............... 623/17.16 |
| 2004/0167534 A1 | 8/2004 | Errico |
| 2004/0167537 A1 | 8/2004 | Errico |
| 2004/0176773 A1 | 9/2004 | Zubok |
| 2004/0215198 A1 | 10/2004 | Marnay et al. |
| 2004/0225295 A1 | 11/2004 | Zubok |
| 2005/0015094 A1 | 1/2005 | Keller |
| 2005/0015095 A1 | 1/2005 | Keller |
| 2005/0021040 A1 | 1/2005 | Bertagnoli |
| 2005/0021042 A1 | 1/2005 | Marnay et al. |
| 2005/0027300 A1 | 2/2005 | Hawkins et al. |
| 2005/0033428 A1 | 2/2005 | Keller |
| 2005/0038511 A1 | 2/2005 | Martz et al. |
| 2005/0043740 A1 | 2/2005 | Haid et al. |
| 2005/0043800 A1 | 2/2005 | Paul et al. |
| 2005/0055029 A1 | 3/2005 | Marik et al. |
| 2005/0055031 A1 | 3/2005 | Lim |
| 2005/0055098 A1 | 3/2005 | Zdeblick |
| 2005/0071013 A1 | 3/2005 | Zubok |
| 2005/0143749 A1 | 6/2005 | Zalenski et al. |
| 2008/0071293 A1 | 3/2008 | Zalenski |
| 2008/0167680 A1 * | 7/2008 | Voegele et al. ............... 606/206 |

FOREIGN PATENT DOCUMENTS

| | | |
|---|---|---|
| EP | 630615 | 6/1994 |
| FR | 2636227 | 9/1988 |
| FR | 2717068 | 3/1994 |
| WO | 9738634 | 4/1997 |
| WO | 0162136 | 2/2001 |

* cited by examiner

CERVICAL MOTION DISC INSERTER

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases (MMPs). These cytokines and MMPs help regulate the metabolism of the nucleus pulposus cells.

In some instances of disc degeneration disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix. In particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

For the cervical portion of the spine in particular, the leading cause of health issues arises from rupture or degeneration of cervical intervertebral discs. Pain in the upper extremities may be caused by compression of spinal nerve roots by a bulging disc, while neck pain may be caused by both collapse of the disc and by the adverse effects of bearing weight through a damaged, unstable vertebral joint. One conventional method of managing these problems is to remove the problematic disc and replace it with a prosthetic disc that allows for the natural motion between the adjacent vertebrae ("a motion disc").

U.S. Pat. No. 6,113,637 ("Gill") discloses a cervical motion disc having a ball and socket articulation, wherein the trough of the socket has a flat portion. The ball and socket geometry provides pivotal motion while the flat portion of the trough allows the ball to slide, thereby providing some translation motion. Gill further discloses a method of inserting the motion disc whereby an inserting device engages the ball and socket components to fix the spatial relationship between the components. The components are then inserted into the disc space in this fixed spatial relationship. Therefore, during the entire insertion procedure, the original spatial relationship may be maintained.

US Patent Publication No. 2005-0143749 (Zalenski) discloses a method and apparatus assisting safe, one-handed insertion of the cervical motion disc. An implant implantation device (or inserter) has a frame which includes a trigger mechanism, an outer sleeve mechanically coupled to the frame, an inner shaft having a grabber for mechanically engaging an implant, the inner shaft slidably disposed within the outer sleeve, and a retaining element disposed over the inner shaft for directing the grabber toward a closed position. An implant clip has a first member, a second member pivotally coupled to the first member, a first implant holder pivotally coupled to the first member, the coupling causing the implant clip to have a closed position and an open position, and a second implant holder, the second implant holder pivotally coupled to the second member, a surface of the first implant holder and a surface of the second implant holder remaining substantially parallel to each other while the first member and the second member pivot between the closed position and the open position.

SUMMARY OF THE INVENTION

The present invention provides a novel inserter for inserting a cervical motion disc. The inserter of the present invention features a pair of projections that are adapted to move slidably and transversely relative to one another (like an adjustable wrench) in order to engage a proximal attachment surface of a prosthetic cervical motion disc. Thus, the present invention does not rely upon any pivoting movement in the gripping portions of the inserter.

Therefore, in accordance with the present invention, there is provided a cervical motion disc inserter comprising:
  a. a longitudinal shaft having a distal end portion comprising
    i. a first medial surface having a first recess therein,
    ii. a first transverse surface extending transversely from the medial surface, and
    iii. a distal end forming a first projection, and
  b. an engagement element comprising:
    i. a second medial surface opposing the first medial surface of the distal end portion of the longitudinal shaft,
    ii. an alignment pin extending transversely from the second medial surface and slidably received within the first recess,
    iii. a distal end forming a second projection.

Also in accordance with the present invention, there is provided a cervical motion disc inserter comprising:
  a) a longitudinal shaft having a distal end portion comprising a first transverse surface and a first projection,
  b) an engagement element comprising a distal end portion comprising a second transverse surface and a second projection, and
  c) means for providing relative translation of the first transverse upon the second transverse surface.

Also in accordance with the present invention, there is provided an assembly for use in cervical disc surgery, comprising:
  a) a prosthetic cervical motion disc having a proximal end having an attachment surface, and b) the inserter of claim 10,
wherein the first and second projections engage the attachment surface of the cervical motion disc.

Also in accordance with the present invention, there is provided a cervical motion disc inserter comprising:
- a) a longitudinal shaft having a distal end portion comprising a first transverse surface and a first projection,
- b) an engagement element comprising a distal end portion comprising a second transverse surface and a second projection, wherein the first transverse surface is adapted to translate upon the second transverse surface and thereby adjust a distance between the first and second projections.

Also in accordance with the present invention, there is provided a cervical motion disc inserter comprising:
- a. a longitudinal shaft having a distal end portion comprising a first medial surface and a first projection,
- b. an engagement element comprising a distal end portion comprising a second medial surface and a second projection, wherein the first medial surface opposes the second medial surface,
wherein the distal portion of the longitudinal shaft and the distal portion of the engagement element form a set of spring-loaded jaws.

Also in accordance with the present invention, there is provided an assembly for use in cervical intervetebral disc surgery, comprising:
- a) a prosthetic cervical motion disc comprising a proximal end having an attachment surface, and
- b) a cervical motion disc inserter comprising:
    - i) a longitudinal shaft having a distal end portion comprising a first medial surface and a first projection,
    - ii) an engagement element comprising a distal end portion comprising a second medial surface and a second projection, wherein the first medial surface opposes the second medial surface,
wherein the distal portion of the longitudinal shaft and the distal portion of the engagement element form a set of spring-loaded jaws, and
wherein the first and second projections engage the attachment surface of the cervical motion disc.

Also in accordance with the present invention, there is provided an assembly for use in cervical intervetebral disc surgery, comprising:
- a) a prosthetic cervical motion disc comprising a proximal end having an attachment surface, and
- b) an adjustable wrench having a set of spring-loaded jaws, wherein the jaws engage the attachment surface of the cervical motion disc.

DETAILED DESCRIPTION OF THE INVENTION

Now referring to FIGS. 1-4, there is provided a cervical motion disc inserter comprising:
- a) a longitudinal shaft 1 having a proximal end portion 2, and a distal end portion 3 comprising
    - i. a first medial surface 5 having a first recess 97 therein,
    - ii. a first transverse surface 9 extending transversely from the medial surface, and
    - iii. a distal end 11 forming a first projection 13, and
- b) an engagement element 21 comprising:
    - i. a second medial surface 23 opposing the first medial surface of the distal end portion of the longitudinal shaft,
    - ii. an alignment pin 25 extending transversely from the second medial surface and slidably received within the first recess,
    - iii. a distal end 27 forming a second projection 29.

In some embodiments (as shown), the distal end portion of the shaft is integral with the proximal end portion of the shaft.

Figure 3:
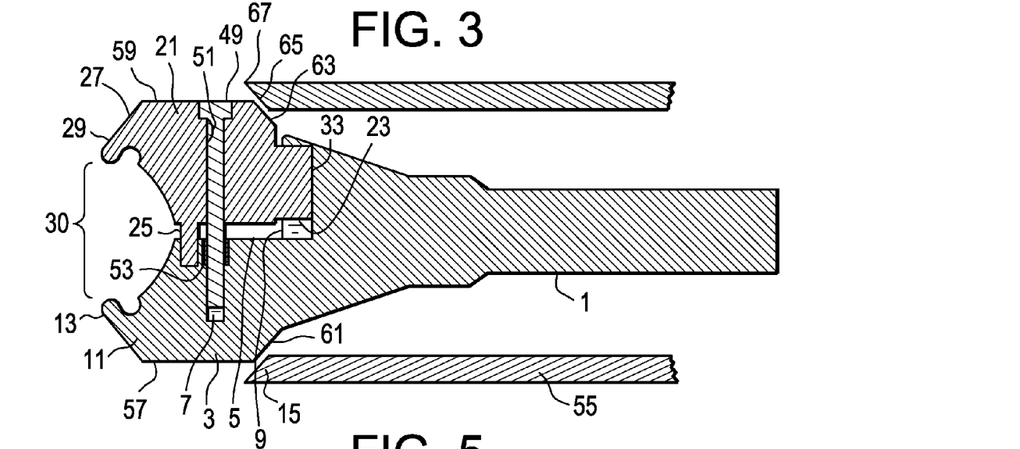
FIG. 3 discloses a cross-section view of the inserter of FIG. 1.

The first and second projections are disposed at the distal end of the inserter and are adapted to engage mating attachment surfaces of a cervical motion disc. Thus, they act together as a set of jaws 30 (as shown in FIG. 3) that can open and shut by virtue of the transverse translation afforded by the inserter, and thereby clamp and release the proximal end portion of the cervical motion disc.

Figure 4:
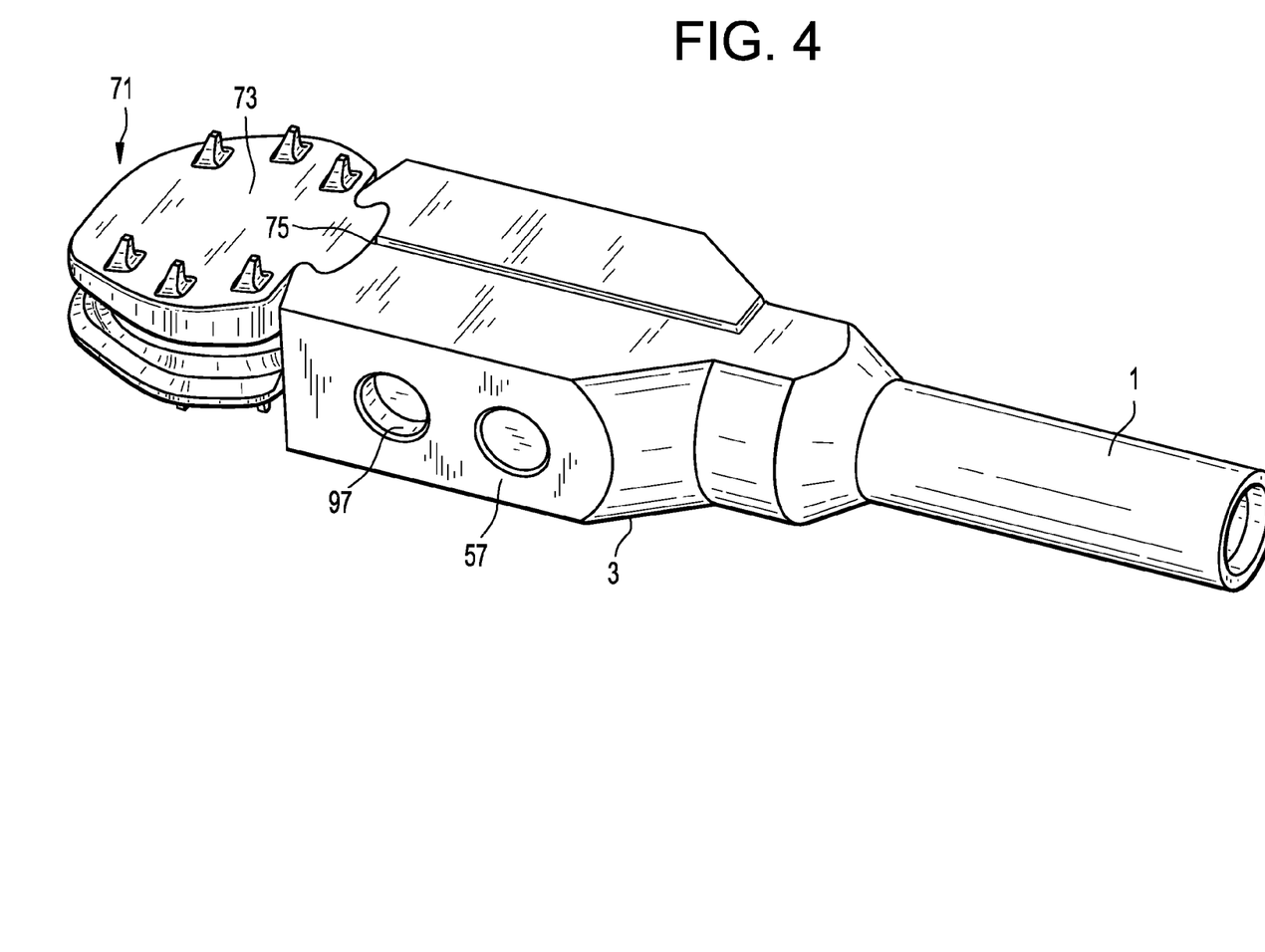
FIG. 4 discloses a perspective view of a second embodiment of the inserter of the present invention clasping a prosthetic cervical motion disc.
Figure 5:
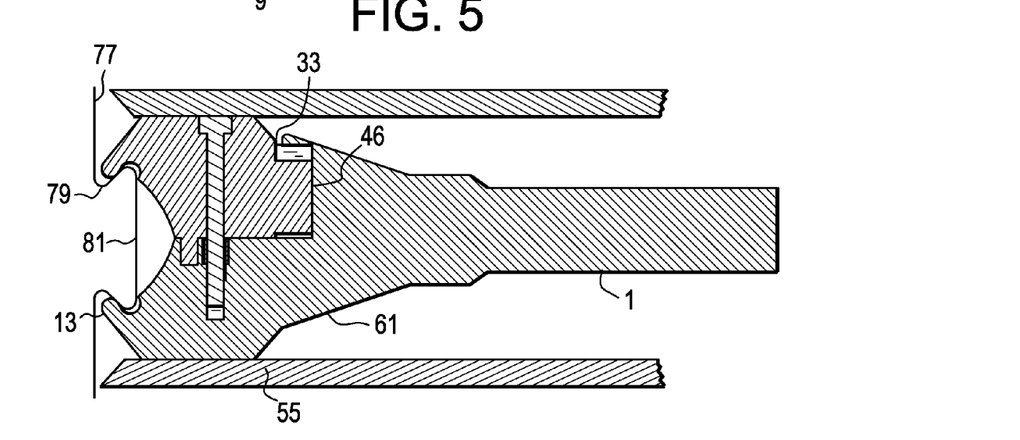
FIG. 5 discloses the distal end portion of the inserter clasped upon the head and neck regions of a cervical motion disc.

An example of this mating engagement is shown in FIGS. 4 and 5. As shown in FIGS. 4 and 5, it is preferred that substantially the entire distal end surface of the both the longitudinal shaft and engagement element are adapted to mate with the proximal end surface of the cervical motion disc.

Now referring back to FIGS. 1-3, the distal end portion of the longitudinal shaft further comprises a first transverse surface 9 extending transversely from the first medial surface and located at the proximal end of the first medial surface, and the engagement element comprises a second transverse surface 33 extending transversely from the second medial surface and located at the proximal end of the second medial surface. The second transverse surface of the engagement element slidably translates on the first transverse surface of the distal end portion of the longitudinal shaft to provide transverse translation of the engagement element.

Figure 1:
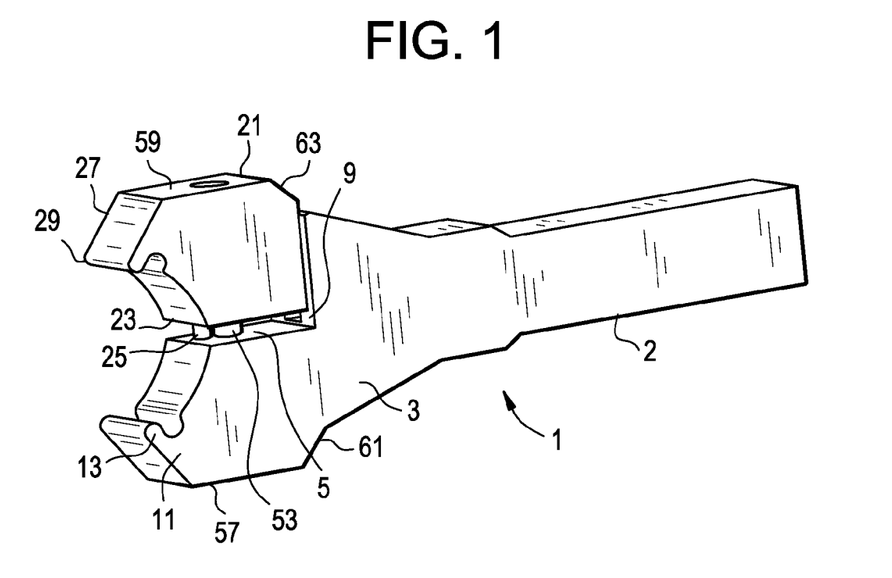
FIG. 1 discloses a perspective view of a basic embodiment of the inserter of the present invention.
Figure 2:
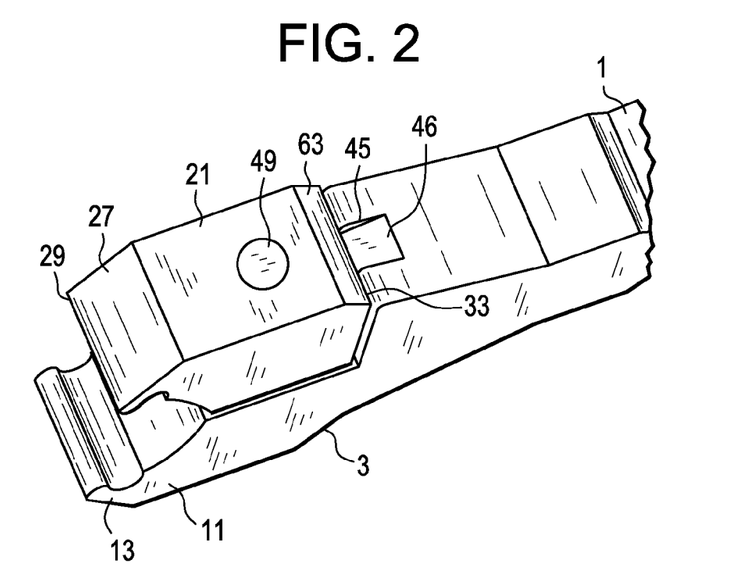
FIG. 2 discloses a perspective view of the distal end portion of the inserter of FIG. 1.

The slidable translation of one transverse surface upon another guides the movement of the engagement element vis-à-vis the shaft. In preferred embodiments, the transverse surface of the distal end portion of the longitudinal shaft has a recess 45 for closely receiving a projection 46 of the transverse surface of the engagement element. The recess has a width that is substantially similar to the width of the transverse surface of the engagement element, but has a length that is slightly longer than the transverse surface of the engagement element, thereby guiding the desired transverse translation.

Also in FIGS. 1-3, the first medial surface of the distal end portion of the longitudinal shaft further comprises a second recess 7 and the engagement element further comprises a flange 49 having a substantially cylindrical surface 51 extending from the second medial surface and a compression spring 53 received upon the substantially cylindrical surface of the flange, wherein the flange and compression spring of the engagement element are received within the second recess of the first medial surface of the distal end portion of the longitudinal shaft.

Figure 6:
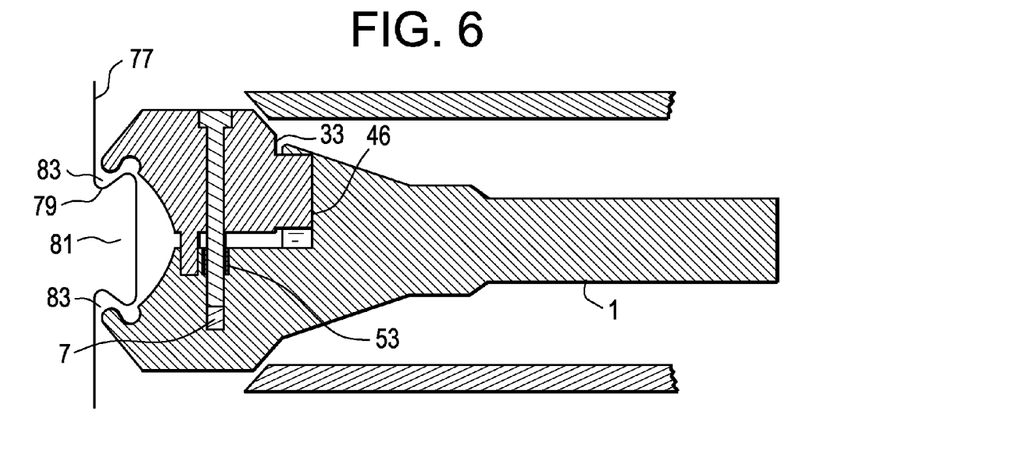
FIG. 6 discloses the distal portion of the inserter in the open jaw configuration surrounding the head and neck regions of a cervical motion disc.

The first function of the compression spring is to provide a first "open jaw" configuration for the distal end portion of the inserter, as shown in FIG. 6. The open jaw configuration allows the surgeon to place the jaw of the inserter around the proximal end portion of the cervical motion disc. The second function of the compression spring is to allow a second "closed jaw" configuration for the distal end portion of the inserter when the annular component 55 is slid over the lateral surface of the distal end portion of the inserter, as shown in FIG. 5. The closed jaw configuration allows the surgeon to clasp the jaw of the inserter upon the proximal end portion of the cervical motion disc. Once the jaw is clasped upon the motion disc, the surgeon may transfer the motion disc to the patient and inserter the motion disc into the patient's cervical disc space. Once the prosthetic disc has been implanted, the surgeon may withdraw the annular component from the inserter, thereby releasing the jaw to its open configuration and allowing removal of the inserter from the patient.

Now referring back to FIGS. 1-3, the distal end portion of the longitudinal shaft further comprises a first lateral surface 57, and the engagement element further comprises a second lateral surface 59, and wherein the first lateral surface is disposed essentially parallel to the second lateral surface.

The parallel nature of the lateral surfaces of the distal end portion of the inserter allows the annular component to have a simple cylindrical inner diameter, as the cylindrical inner surface of the annular component will align itself to the parallel disposition of the lateral surfaces. The parallel nature of the lateral surfaces also allows insertion of the inserter through a minimum diameter portal in the patient's neck.

The open and closed nature of the jaws as a function of the annular component position is demonstrated in FIGS. 5 and 6, wherein the first and second lateral surfaces define a first distance therebetween when the compression spring is relaxed (FIG. 6) and a second distance therebetween when the compression spring is compressed (FIG. 5), and wherein the inserter further comprises an annular component 55 disposed around the first and second lateral surfaces, the annular component having an inner diameter no greater than the first distance.

Now referring back to FIGS. 1-3, a proximal portion of the first lateral surface forms a first chamfer 61, and the second medial surface and second lateral surface intersect to form a second chamfer 63. As shown in FIG. 3, the annular component has a tapered distal end chamfer 65 that narrows to a lateral point 67. Preferably, the angle of the chamfers on the shaft and engagement element is substantially equal to the angle of the chamfer upon the distal end of the annular component. The equality of angles is preferable for two reasons. First, it allows for a more smooth engagement of the components and thereby reduces wear. Second, in this condition, the chamfer at the distal end of the annular component can press down upon the chamfers of the shaft and engagement element as it advances distally, and thereby push the engagement element medially towards the first medial surface of the shaft. This medial translation of the engagement element will desirably change the jaw configuration from an open to a closed configuration.

Preferably, the distance between the chamfers in the open jaw configuration is substantially similar to the inner diameter of the annular component.

FIG. 5 discloses the distal end portion of the inserter clasped upon the proximal end portion of a cervical motion disc. In particular, FIG. 5 discloses an assembly for use in cervical disc surgery, comprising:

a) a prosthetic cervical motion disc 71 having a proximal end 73 having an attachment surface 75, and b) a distal portion of the inserter of the present invention, wherein the first and second projections of the inserter engage the attachment surface of the cervical motion disc.

As shown in FIG. 5, the attachment surface of the cervical motion disc preferably comprises a base surface 77, a neck region 79 extending proximally from the base surface, and an enlarged head region 81 formed proximally upon the neck region. Because the neck region is thinner than the more proximal and distal regions of the prosthetic disc, the neck region of the cervical motion disc defines bilateral grooves 83. Accordingly, the first and second projections of the inserter engage the attachment surface of the cervical motion disc in a bilateral tongue-and-groove configuration at the level of the neck region.

In preferred embodiments, the detailed structure of the inserter, including but not limited to the trigger mechanism, is the same as that described in US Patent Publication No. 2005-0143749 (Zalenski), the specification of which is incorporated by reference in its entirety, In use, the method of implanting a prosthetic cervical disc disclosed in US Patent Publication No. 2005-0143749 (Zalenski), the specification of which is incorporated by reference in its entirety, may be carried out.

Figure 7A:
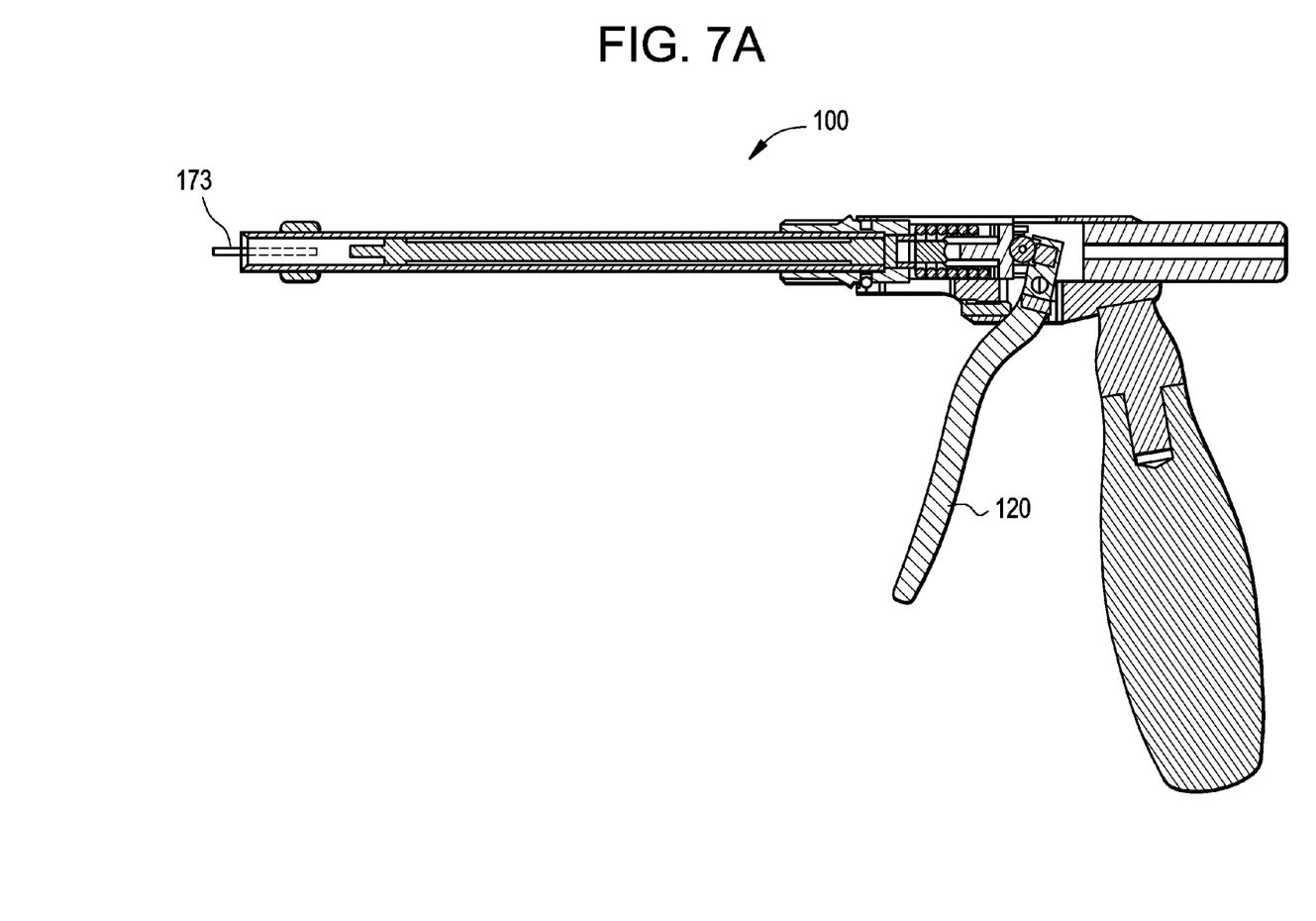
FIGS. 7a-7j disclose instruments, devices and methods of using the present invention.
Figure 7B:
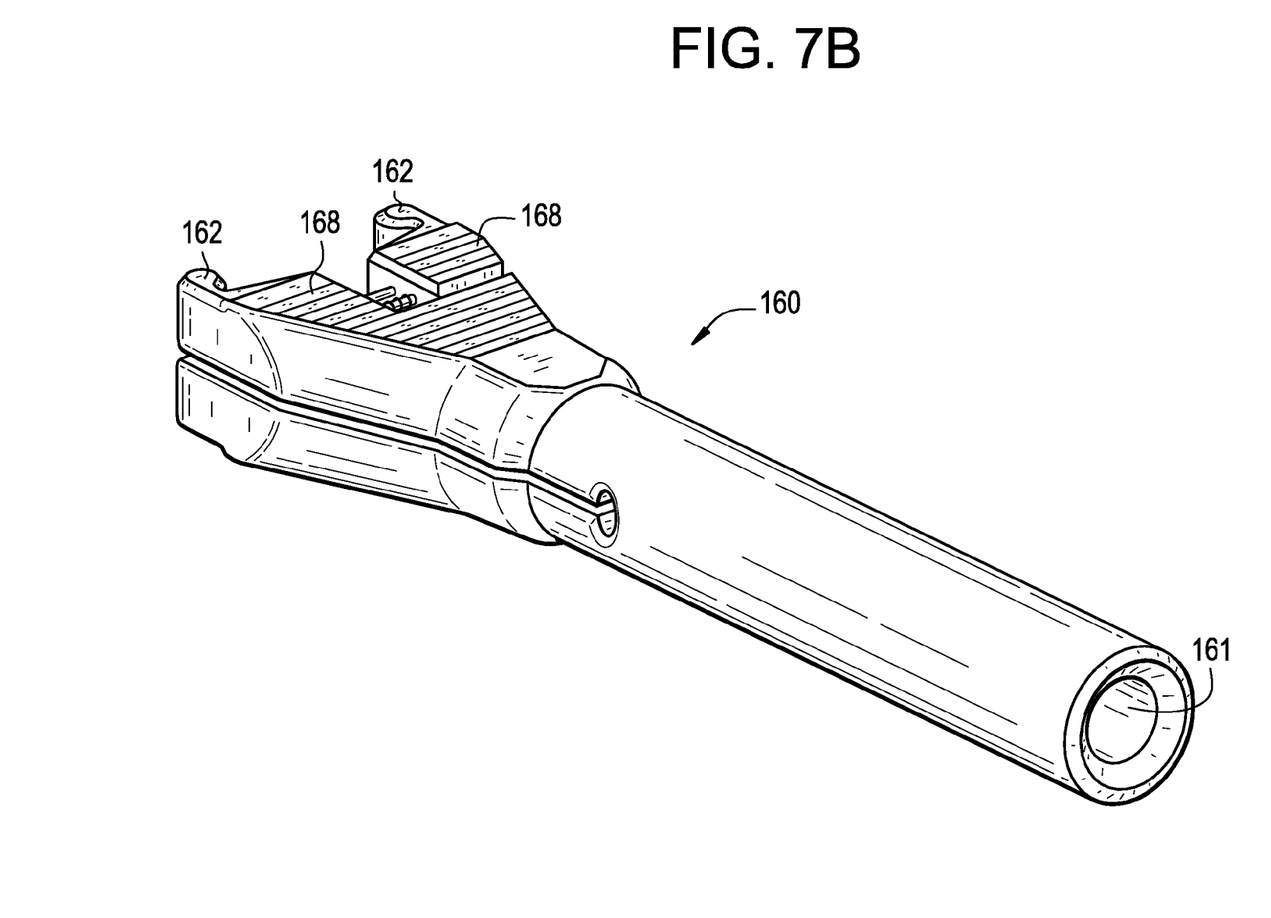
Figure 7C:
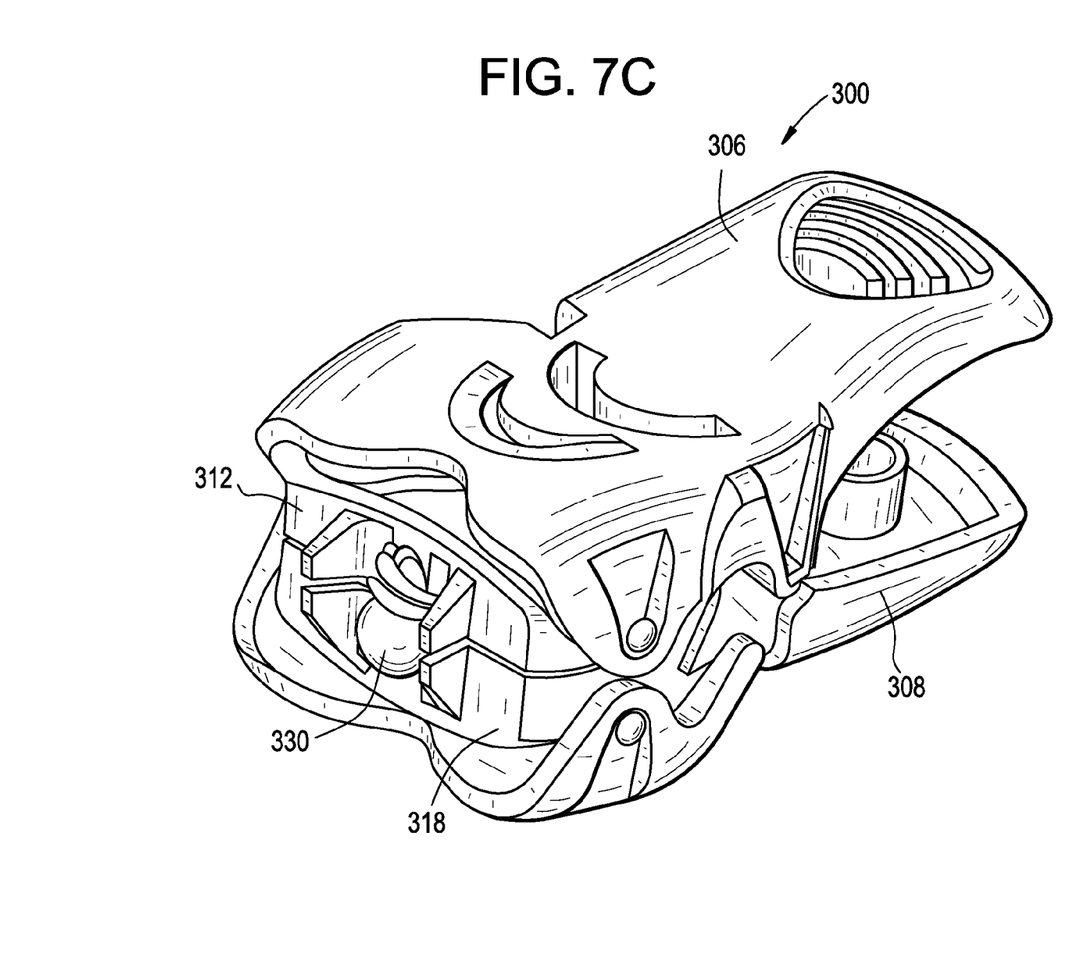
Figure 7D:
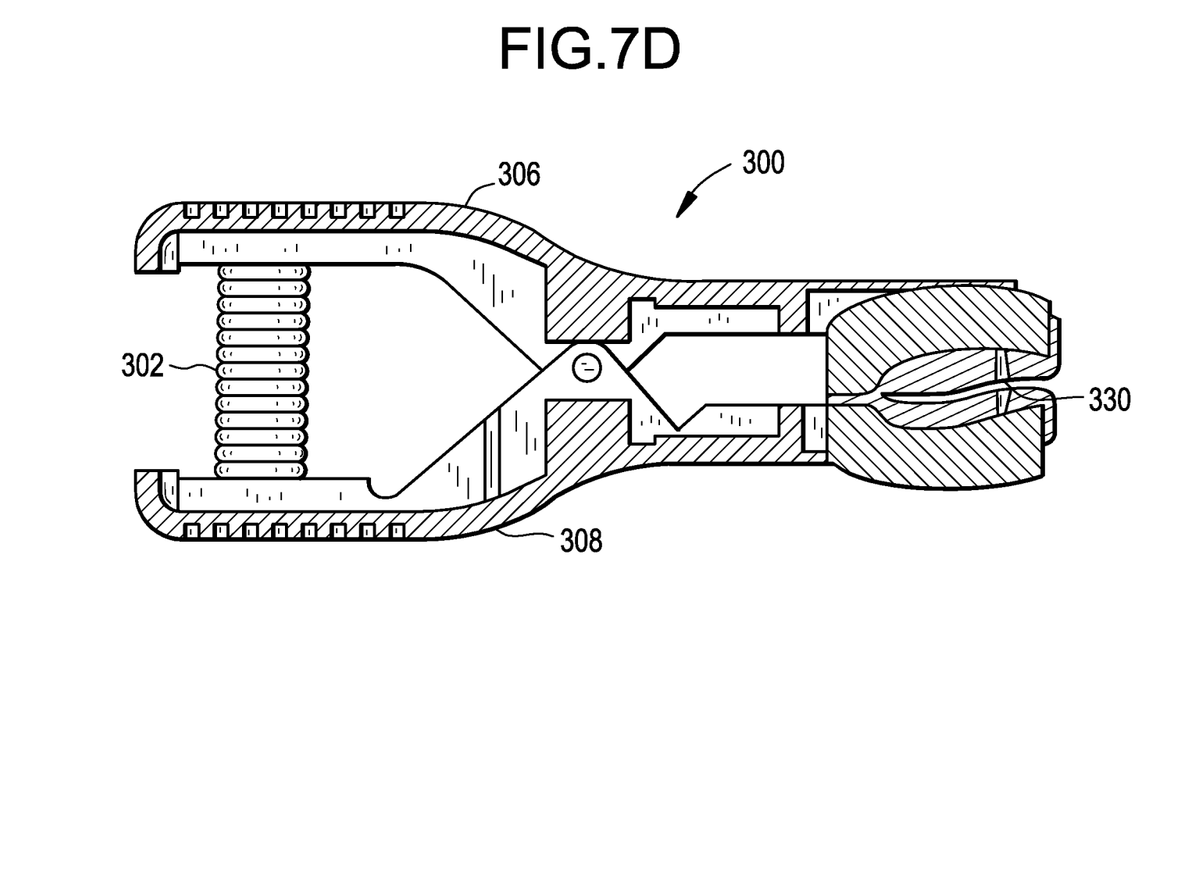
Figure 7E:
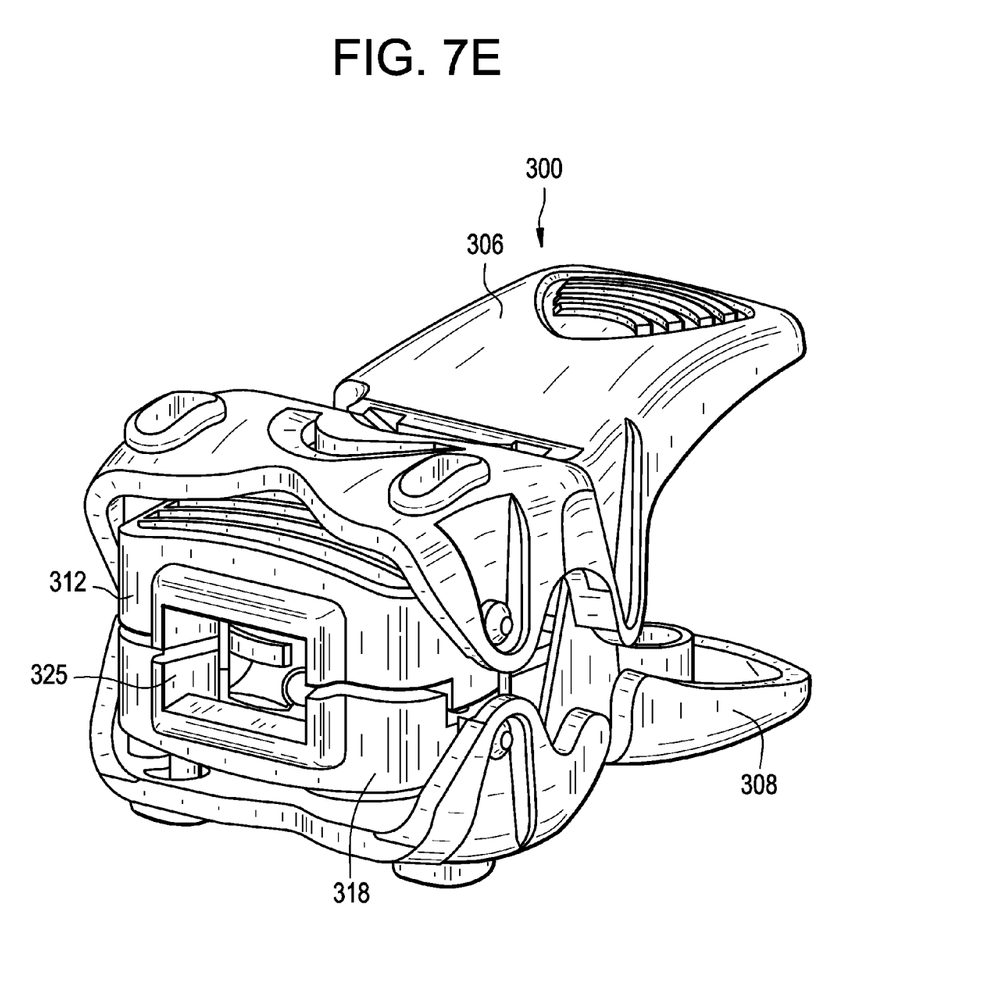
Figure 7F:
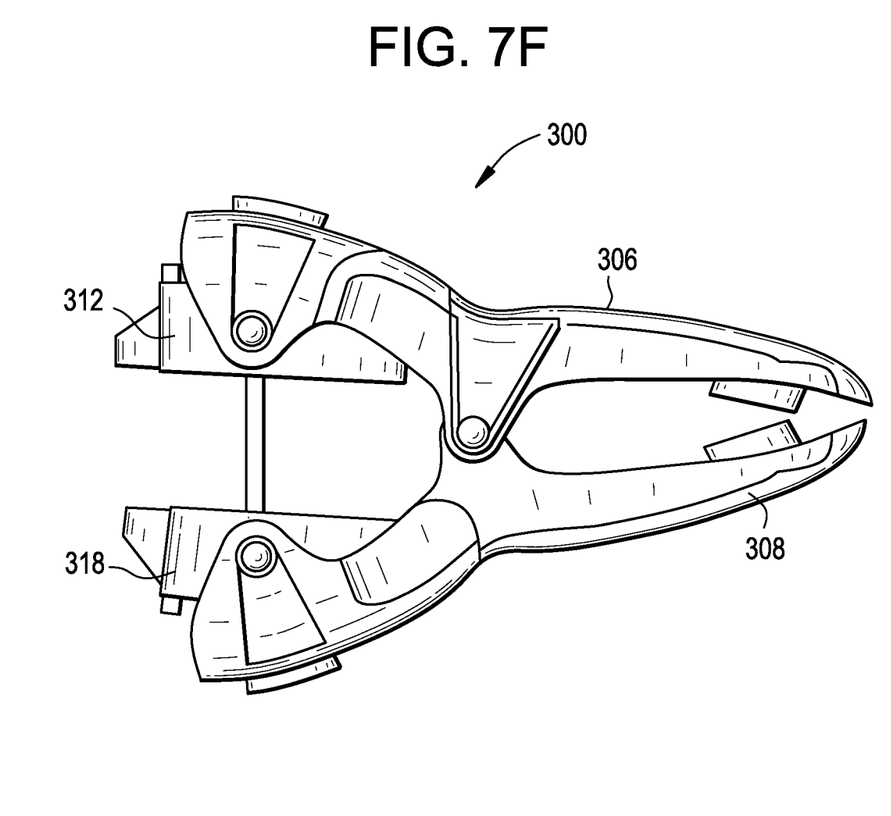

Now referring to FIG. 7 d-f, in operation, a user opens implant clip 300 by depressing and holding opposite portions of shells 306, 308 at opposite ends of spring 302 (FIG. 7d) to an open position (as shown in FIG. 7f). Opened clip 300 is placed over a selected artificial disc 330, causing implant holders 312, 318 to engage artificial disc 330 when shells 306, 308 are released.

Figure 7G:
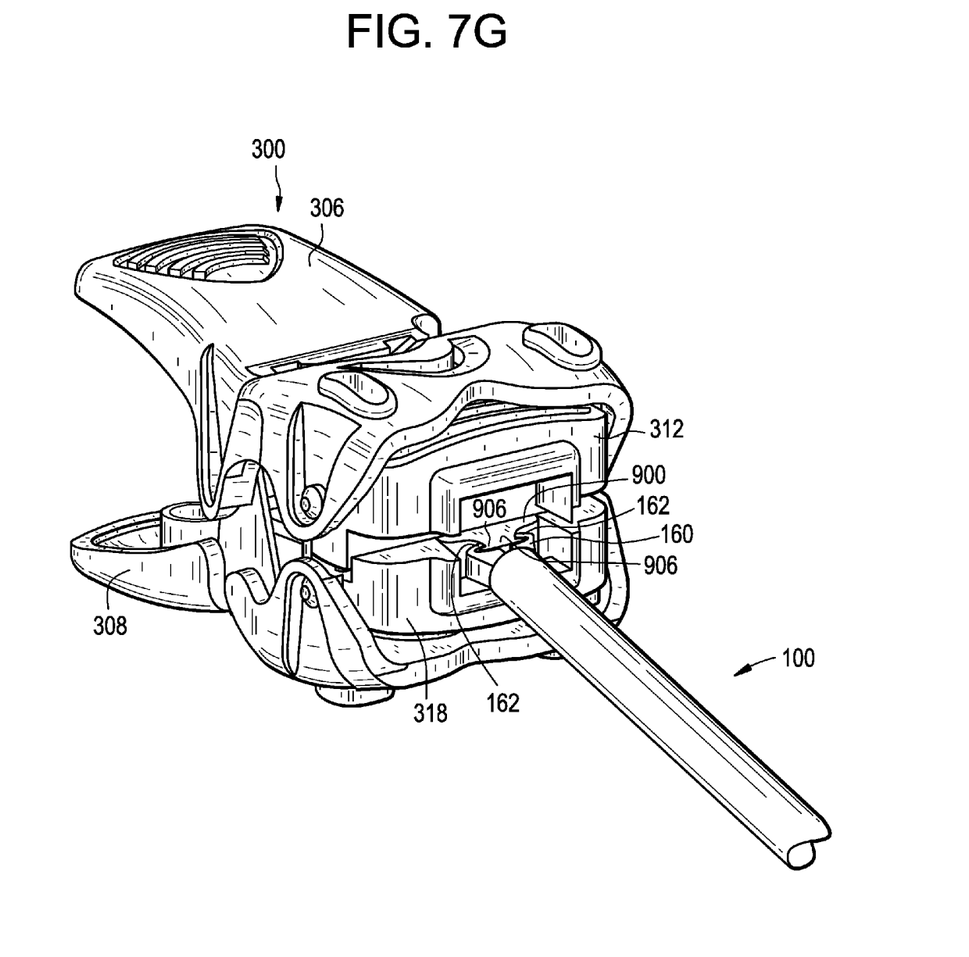
Figure 7H:
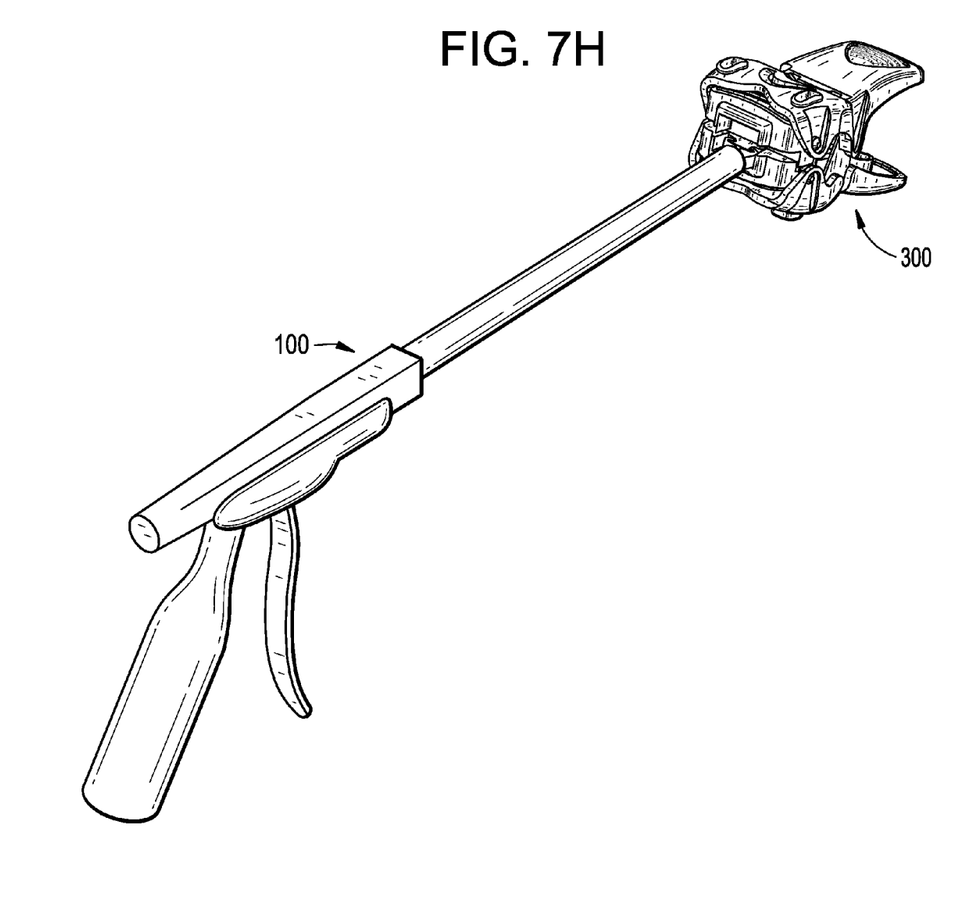

Now referring to FIG. 7b, in one embodiment, the user aligns the jaws 160 of implantation instrument 100 with alignment window 325 on implant clip 300. Now referring to FIG. 7a, once aligned, the user squeezes trigger mechanism 120 on implantation inserter 100, thereby causing projections 162 to be inserted over engagement grooves 906 on artificial disc 900 (as shown in FIG. 7g).

Figure 7I:
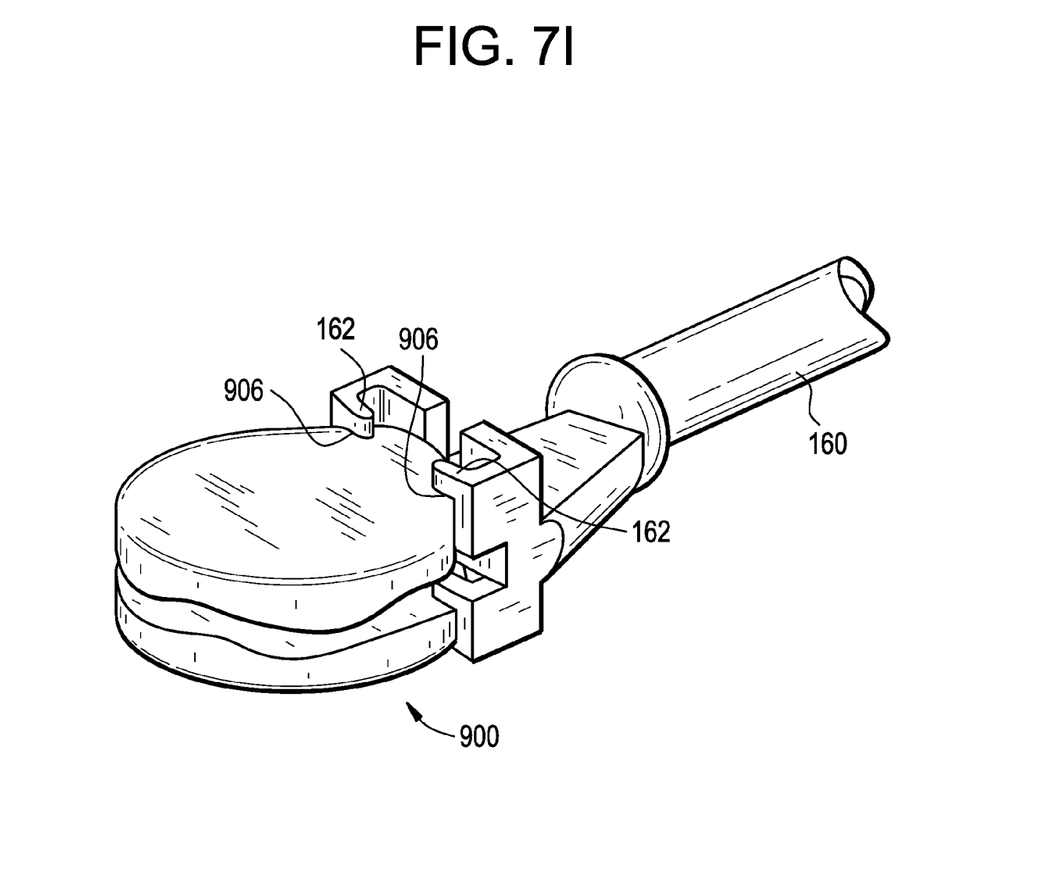

Now referring to FIG. 7i, there is a slightly different inserter (without the annular component) performing the same function. Once projections 162 are inserted over engagement grooves 906, the user releases trigger mechanism 120, causing projections 162 to engage engagement grooves 906 on artificial disc 900 (FIG. 7g). The user removes implant clip 300 from artificial disc 900 by opening and removing implant clip 300 from the now engaged artificial disc 900, as shown in FIG. 7j.

Figure 7J:
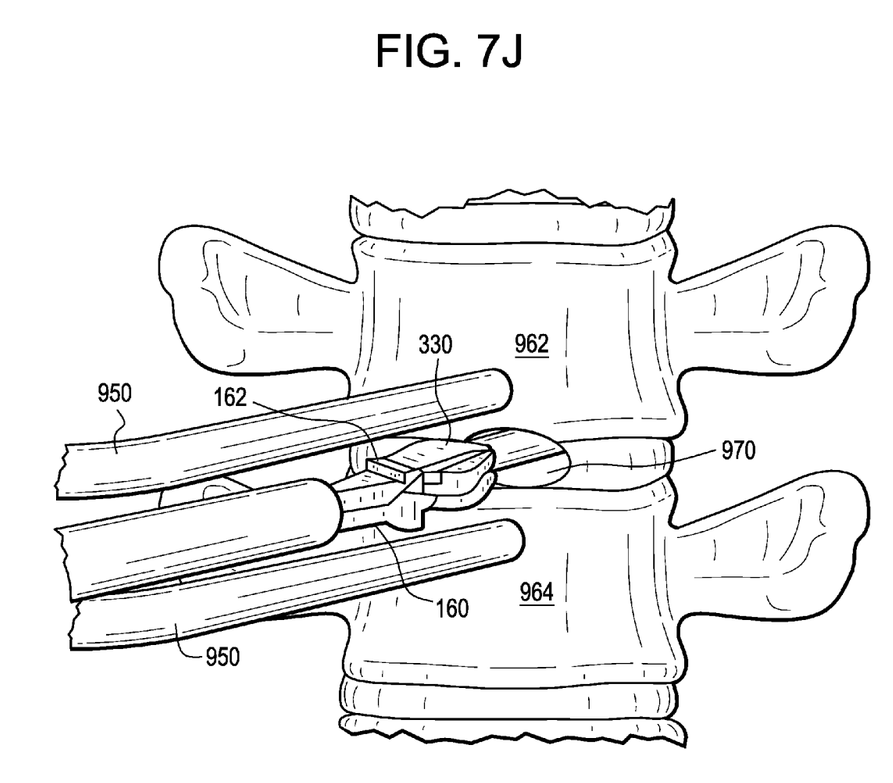

Now referring to FIG. 7j, distraction instrument 950 is inserted over pins (not shown) that are secured into vertebral bodies 962, 964. Artificial disc 330 is passed between the forks of distraction instrument 950 using implantation inserter 100 (as shown in FIG. 7a). Once artificial disc 330 is in a desired location within prepared disc space 970, the user squeezes trigger mechanism 120 (FIG. 7a) which releases artificial disc 330 in prepared disc space 970. The user can determine the desired position by observing cephalad markers 168 (FIGS. 7c-d) located on a surface of the jaws 160. In an alternative embodiment, implantation instrument 100 can include a depth control member 173 (FIG. 7a) such that artificial disc 330 can be inserted into prepared disc space 970 at a predetermined depth.

Lastly, the inserter 100 and distraction instrument 950 are removed, causing superior vertebra 962 and inferior vertebra 964 to engage artificial disc 330.

We claim:

1. A cervical motion disc inserter comprising:
   a. a longitudinal shaft having a distal end portion comprising
      i. a first medial surface having a first recess therein,
      ii. a first transverse surface extending transversely from the medial surface, and
      iii. a distal end forming a first projection, and
   b. an engagement element comprising:
      i. a second medial surface opposing the first medial surface of the distal end portion of the longitudinal shaft,
      ii. an alignment pin extending transversely from the second medial surface and slidably received within the first recess,
      iii. a distal end forming a second projection,
   wherein the first medial surface of the distal end portion of the longitudinal shaft further comprises a second recess, and the engagement element further comprises a flange having a substantially cylindrical surface extending from the second medial surface and a compression spring received upon the substantially cylindrical surface of the flange, wherein the flange and compression spring of the engagement element are received within the second recess of the first medial surface of the distal end portion of the longitudinal shaft.

2. The inserter of claim 1 wherein the first and second projections are adapted to engage attachment surfaces of a cervical motion disc.

3. The inserter of claim 1 wherein the distal end portion of the longitudinal shaft further comprises a first transverse surface extending transversely from the first medial surface and proximal of the medial surface, and wherein the engagement element comprises a second transverse surface extending transversely from the second medial surface and proximal of the second medial surface, and wherein the second transverse surface of the engagement element slidably translates on the first transverse surface of the distal end portion of the longitudinal shaft to provide transverse translation of the engagement element.

4. The inserter of claim 1 wherein the distal end portion of the longitudinal shaft further comprises a first lateral surface, and the engagement element further comprises a second lateral surface, and wherein the first lateral surface is disposed essentially parallel to the second lateral surface.

5. The inserter of claim 4 wherein the first and second lateral surfaces define a first distance therebetween when the compression spring is relaxed and a second distance therebetween when the compression spring is compressed, and wherein the inserter further comprises an annular component disposed around the first and second lateral surfaces, the annular component having an inner diameter no greater than the first distance.

6. The inserter of claim 5 wherein the first medial surface and first lateral surface intersect to form a first chamfer, and wherein the second medial surface and second lateral surface intersect to form a second chamfer.

7. The inserter of claim 6 wherein the annular component has a tapered distal end that narrows to a lateral point.

8. The inserter of claim 3 wherein the transverse surface of the distal end portion of the longitudinal shaft has a recess for closely receiving a projection of the transverse surface of the engagement element.

* * * * *